(12) United States Patent
Li (10) Patent No.: US 7,361,133 B2
(45) Date of Patent: Apr. 22, 2008

(54) METHODS OF DETECTION UTILIZING MODIFIED BACTERIOPHAGE

(75) Inventor: Min Li, Lutherville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/726,624

(22) Filed: Nov. 30, 2000

(65) Prior Publication Data

US 2001/0019820 A1 Sep. 6, 2001

Related U.S. Application Data

(62) Division of application No. 08/861,572, filed on May 22, 1997, now Pat. No. 6,190,856.

(51) Int. Cl.
*C40B 10/00* (2006.01)
(52) U.S. Cl. ................. 506/1; 435/6; 530/300
(58) Field of Classification Search .......... 435/4, 435/5, 7.1, 7.21, 7.23, 320.1, DIG. 1, DIG. 4, 435/DIG. 15, 6; 530/344, 300, 399, 412, 530/413
See application file for complete search history.

(56) References Cited

U.S. PATENT DOCUMENTS

| | | | | |
|---|---|---|---|---|
| 4,851,331 A | | 7/1989 | Vary et al. | 435/6 |
| 5,270,170 A | * | 12/1993 | Schatz et al. | 435/7.37 |
| 5,432,018 A | | 7/1995 | Dower et al. | 435/5 |
| 5,489,717 A | * | 2/1996 | Bigge et al. | 570/183 |
| 5,627,024 A | * | 5/1997 | Maruyama et al. | 435/5 |
| 5,922,545 A | * | 7/1999 | Mattheakis et al. | 435/6 |
| 6,190,856 B1 | * | 2/2001 | Li | 435/4 |
| 6,242,568 B1 | * | 6/2001 | Barbas, III et al. | 520/350 |

OTHER PUBLICATIONS

Goodson et al., Proc. Natl. Acad. Sci. 91:7129-7133 (1994).*
Zhou et al., Journal of Neurochemistry 66(2):620-628 (1996).*

* cited by examiner

*Primary Examiner*—Jon D. Epperson
*Assistant Examiner*—Jeffrey S. Lundgren
(74) *Attorney, Agent, or Firm*—Banner & Witcoff, Ltd.

(57) ABSTRACT

Viruses expressing ligands on their surfaces are used as a detection means for the related polypeptide which binds the ligand. Multiple copies of the ligand can be expressed on the viral surface. These viruses may be used to detect polypeptides, cells, receptors and channel proteins.

4 Claims, 7 Drawing Sheets

A

Mag-4.1   LNDWFITYI

Mag-4.2   LEAWFLQYI

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
          (A) LENGTH: 50 amino acids
          (B) TYPE: amino acid
          (C) STRANDEDNESS: single
          (D) TOPOLOGY: linear (ii) MOLECULE TYPE: None (xi) SEQUENCE DESCRIPTION: SEQ ID NO: 1:

Ala Ala Ala Cys Leu Glu Pro Tyr Thr Ala Cys Asp Leu Ala Pro Pro
1               5                   10                  15

Ala Gly Thr Thr Asp Ala Ala His Pro Gly Arg Ser Val Val Pro Ala
            20                  25                  30

Leu Leu Pro Leu Leu Ala Gly Thr Leu Leu Leu Leu Glu Thr Ala Thr
        35                  40                  45

Ala Pro
    50

(2) INFORMATION FOR SEQ ID NO: 2:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: None (xi) SEQUENCE DESCRIPTION: SEQ ID NO: 2:

Leu Asn Asp Trp Phe Ile Thr Tyr Ile
1               5

(2) INFORMATION FOR SEQ ID NO: 3:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: None (xi) SEQUENCE DESCRIPTION: SEQ ID NO: 3:

Leu Glu Ala Trp Phe Leu Gln Tyr Ile
1               5

(2) INFORMATION FOR SEQ ID NO: 4:

(i) SEQUENCE CHARACTERISTICS:
          (A) LENGTH: 15 amino acids
          (B) TYPE: amino acid
          (C) STRANDEDNESS: single
          (D) TOPOLOGY: linear (ii) MOLECULE TYPE: None (xi) SEQUENCE DESCRIPTION: SEQ ID NO: 4:

Gly Gly Gly Leu Asn Asp Trp Phe Ile Thr Tyr Ile Gly Gly Gly
1               5                   10                  15

(2) INFORMATION FOR SEQ ID NO: 5:

(i) SEQUENCE CHARACTERISTICS:
        (A) LENGTH: 10 amino acids
        (B) TYPE: amino acid
        (C) STRANDEDNESS: single
        (D) TOPOLOGY: linear     (ii) MOLECULE TYPE: None     (xi) SEQUENCE DESCRIPTION: SEQ ID NO: 5:

```
Trp Asp Pro Ala Val Phe Arg Gly Cys Met
1               5                   10
```

(2) INFORMATION FOR SEQ ID NO: 6:

(i) SEQUENCE CHARACTERISTICS:
        (A) LENGTH: 10 amino acids
        (B) TYPE: amino acid
        (C) STRANDEDNESS: single
        (D) TOPOLOGY: linear     (ii) MOLECULE TYPE: None     (xi) SEQUENCE DESCRIPTION: SEQ ID NO: 6:

```
Leu Gly Ser Gly Gly Val Gln Arg Val His
1               5                   10
```

(2) INFORMATION FOR SEQ ID NO: 7:

(i) SEQUENCE CHARACTERISTICS:
        (A) LENGTH: 10 amino acids
        (B) TYPE: amino acid
        (C) STRANDEDNESS: single
        (D) TOPOLOGY: linear     (ii) MOLECULE TYPE: None     (xi) SEQUENCE DESCRIPTION: SEQ ID NO: 7:

```
Met Thr Arg Ala Thr Pro Gly Met Val Phe
1               5                   10
```

(2) INFORMATION FOR SEQ ID NO: 8:

(i) SEQUENCE CHARACTERISTICS:
        (A) LENGTH: 11 amino acids
        (B) TYPE: amino acid
        (C) STRANDEDNESS: single
        (D) TOPOLOGY: linear     (ii) MOLECULE TYPE: None     (xi) SEQUENCE DESCRIPTION: SEQ ID NO: 8:

```
Thr Asn Leu Arg Arg Gly Phe Trp Ile Ile Leu
1               5                   10
```

(2) INFORMATION FOR SEQ ID NO: 9:

(i) SEQUENCE CHARACTERISTICS:
        (A) LENGTH: 11 amino acids
        (B) TYPE: amino acid
        (C) STRANDEDNESS: single
        (D) TOPOLOGY: linear

```
    (ii) MOLECULE TYPE: None (xi) SEQUENCE DESCRIPTION: SEQ ID NO: 9:

Phe Ser Met Asp Ala Trp Phe Leu Gln Tyr Leu
1               5                   10
```

METHODS OF DETECTION UTILIZING MODIFIED BACTERIOPHAGE

This application is a divisional of U.S. Ser. No. 08/861,572, filed May 22, 1997, now U.S. Pat. No. 6,190,856.

BACKGROUND OF THE INVENTION

1. Field of the Invention

The present invention provides improved assays for detection of proteins utilizing virus expressing a ligand for the protein. Such assays can be used in areas wherein traditional immunoassays have previously been utilized.

2. Background Art

Conventional immunoassays rely on the high affinity specific interaction between immunoglobulin and its corresponding epitope. Generally, a variable region of immunoglobulin forms a binding pocket that recognizes either conformation or primary sequence of a given epitope. Because the epitope can be a very small and linear region of a protein, it is common to find that an immunoglobulin recognizes a protein in either native or denatured conformation by binding to a small embedded peptide. Therefore detection agents that can recognize native conformations of peptides, such as receptors, channels, other surface proteins, and extracellular proteins, would be highly useful.

Use of random peptide phage libraries to isolate lead compounds for target proteins has yielded a variety of peptides that recognize specific target proteins with interesting biological activities. Such strategy has provided interesting binding peptides which recognize important proteins including antibodies (Smith, 1985; Cwirla et al., 1990; Scott and Smith, 1990; Kay et al., 1993), streptavidin (Devlin et al., 1990), calmodulin (Dedman et al., 1993), SH3 domain (Sparks et al., 1994), and endoplasmic reticulum protein BiP (Blond-Elguindi et al., 1993). Some of these peptides have yielded important insights into the structure-function of the target protein For example, analysis of peptides that bind to BiP have shown that BiP preferentially binds peptides containing a subset of aromatic and hydrophobic amino acids in alternating positions, suggesting that peptides bind in an extended conformation, with the side chains of alternating residues pointing into a cleft on the BiP molecule (Blond-Elguindi et al., 1993).

N-methyl D-aspartate receptor (NMDAR) channels, found in brain, belong to the superfamily of ligand-gated ion channels, which become selectively permeable to ions upon binding to ligands. The glutamate-mediated channel activity is important for synaptic plasticity, synaptogenesis, and excitotoxicity. NMDA receptors are encoded by at least five genes (NR1, 2A, 2B, 2C, and 2D) and their spliced variants[7]. NR1 is an essential subunit for mediating glutamate-induced channel activity, since a homomultimeric NR1 complex, when expressed in *Xenopus oocytes*, exhibits some of key properties found in native channels. These properties include direct permeability of calcium, voltage dependent $Mg^{2+}$ blockade of the ion channel, and binding sites for modulators such as $Zn^{2+}$, glycine, and polyamines. The other subunits by themselves cannot form a functional channel. However, they coassemble with NR1 to form heteromultimers which increase the expression level and channel diversity. The NR1 polypeptide can be divided into two regions: an extracellular amino-terminal domain containing the putative agonist binding site, and a hydrophobic core region with multiple transmembrane segments which participate the formation of the ion conducting pathway. Although several classes of compounds have been found to modulate the NMDA receptor, at the molecular level little is known in terms of amino acid residues that are responsible for the interaction. To better understand the physiological roles of NMDA receptors with different subunit composition or to detect NMDA receptors in samples, it would be helpful to develop specific ligands that are capable of distinguishing different subunits.

Excitotoxic mechanisms have a well established role in the pathogenesis of neuronal injury following acute CNS insults such as ischaemia and trauma. Increasing evidence now supports their roles in chronic neurodegenerative disorders such as motor neuron diseases (MND). Although the molecular mechanisms underlying excitotoxic neuronal injury are still being elucidated, a large body of evidence indicates that the cascade of events resulting from elevation of intracellular free calcium is likely to play a major role, which is thought to be mediated by NMDA receptor and voltage-gated calcium channels. NMDA receptor has several very important properties of relevance to excitotoxicity, particularly, the ability to permeate calcium ions. Thus, understanding of NMDA receptor properties at the molecular level and development of reagents that specifically modulate these receptors can be of importance for understanding excitotoxicity resulted diseases and providing potential leads which could facilitate future treatments. By further improving the affinity and stability of NMDA receptor-specific ligands, their potential neuronal protective activity can be improved.

The present invention provides new procedures which use bacterial virus (including bacteriophage) as a detective reagent, in a way comparable to primary antibody in immunoassays, to monitor the expression of receptor and channels in mammalian cells. Conversely, the phage binding described herein requires the corresponding receptor in proper conformation to present the binding pocket for the peptide to bind. Because the conformation of receptor binding pocket is critical for the peptide binding, peptide-receptor target interaction per se can have higher specificity than that of some antibody-receptor interaction. In search of novel peptides that modulate receptor activity, phage clones with specific interacting peptides from random peptide libraries have been isolated by panning selection, which is often based on the multivalent interaction between the phage particle and target receptor. These assays provide an improved way to detect protein expression and to study peptide-receptor interaction at the molecular level.

BRIEF DESCRIPTION OF THE DRAWINGS

The file of this patent contains at least one drawing executed in color. Copies of this patent with color drawings are provided to the Patent and Trademark Office with payment of the necessary fee.

FIG. 1A-1C. Isolation of Mag-4 peptides that specifically associate with N-NR1. FIG. 1A. Amino acid sequence alignment. Two phage clones, Mag-4.1 and Mag-4.2, specifically association with N-NR1 were isolated by panning selection (see Experimental Protocols). The amino acid sequence was deduced and aligned. FIG. 1B Binding specificity of Mag-4.1 peptides to the H2-terminal domain of glutamate receptor. Phage ELISA experiments were carried out using N-NR1, N-NR1.sp1, and N-GluR1. Experimental procedures were described in Experimental Protocols. The dash bars indicate wells coated with bovine serum albumin (BSA) only, white bars: BSA plus mAb8610; black bars: BSA, mAb8610 plus the captured fusion proteins for N-NR1, N-NR1.sp1, or N-GluR1 (as indicated). Experiments were carried out in triplicate. Error bars indicate the SD FIG. 1C Inhibition of Mag-4.1 phage binding by synthetic Mag-4.1 peptide. The ability of synthetic HPLC-purified Mag-4.1 peptide (GGGLNDWFITYIGGG) (SEQ ID NO:4) to compete with the Mag-4.1 phage binding to N-NR1 fusion protein was determined by phage ELISA The vertical axis indicates the relative binding comparing to the signal obtained without adding the peptide inhibitors. The horizontal axis indicates concentration of the peptides added in mM (as indicated).

FIG. 2. Specific detection of N-NR1 protein by phage-overlay. Crude extracts containing fusion proteins of N-NR1 and N-NR2A at 1:5 ratio were fractionated on SDS-PAGE and transferred onto a nitrocellulose filter. The immobilized proteins were subjected to a denaturation-renaturation procedures (see Experimental Protocol). The renatured protein were detected by either monoclonal antibody 8610 (mAb8610) left panel) or Mag-4.1 phage (right panel). Lanes 1, 2, 3 and 4 contain decreasing amounts of N-NR1 fusion protein (100 ng, 20 ng, 4 ng, and 0.8 ng).

FIGS. 4A-4C. Double stain of N-NR1 protein by mAb8610 and Mag-4.1 phage. N-NR1 positive and N-NR1 negative cells were mixed at ratio 1:1 and allowed to grow on gelatin-coated cover glass. The live cells were first incubated with Mag-4.1 phage. After fixation, the cells were incubated with mAb8610 (mouse) specific to the epitope on fusion protein and anti-phage antibody (rabbit). The antibody binding was then detected by goat-anti-mouse (Texas-red) and goat-anti-rabbit (fluorescein, green). A same area of cells were visualized by (FIG. 4A) Nomaski, (FIG. 4B) mAb8610; and (FIG. 4C) Mag-4.1.

FIGS. 5A-5E. Detection of the N-NR1 protein by FACS. CHO cells were stained with Mag-4.1 phage followed by rabbit anti-phage antibody and fluorescein-labeled secondary antibody (see FIG. 4 legend and Experimental Protocol). Vertical axis is relative cell number, horizontal axis is relative intensity of green fluorescence. (FIG. 5A) CHO cells; (FIG. 5B) CHO cells expressing low level of N-NR1 protein; (FIG. 5C) same as B, but stained in the presence of 500 mM of Mag-4.1 peptide; (FIG. 5D) a 1:1 mixture of CHO cells expressing high and low levels of N-NR1 protein; (FIG. 5E) same as FIG. 5D, but in the presence 500 mM of Mag-4.1 peptide.

FIGS. 6A and 6B. Detection of functional NMDA receptor by Mag-4.1 phage. HEK cells were cotransfected with plasmids expressing NR1 and NR2A cDNAs to form functional NMDA receptor channels (Li et al., 1996). At 48 hours after transfection, the cells were subjected to phage-immunostain using Mag-4.1. The phage binding was visualized by HPR-conjugated antibody (see Experimental Protocol). Same area of stained cells was shown in low magnification (FIG. 6A) or high magnification (FIG. 6B).

DETAILED DESCRIPTION OF THE INVENTION

The present invention provides a method of detecting the presence of a polypeptide in a sample comprising contacting with the sample a detectable virus expressing on its surface a ligand for the polypeptide and detecting binding of the virus to the sample, thus detecting the presence of the polypeptide in the sample.

By "sample" is meant a sample wherein the selected polypeptide in the sample is not an isolated polypeptide, some examples of such a sample including a protein homogenate from a cell, tissue or animal; cells; tissue section; biological or clinical sample such as blood, urine, saliva; any other sample to be tested for presence of contaminants comprising proteins (e.g., water sample, food sample). For example, the presence of a microbe can be detected in a food, water or clinical sample be detecting the presence of a protein, intracellular, surface or extracellular, that is a component of the microbe in the sample.

As used in the specification and in the claims, "a" can mean one or more, depending upon the context in which it is used.

The terms "polypeptide" and "peptide" refer to a polymer of amino acids and includes full-length proteins and fragments thereof By "selected" polypeptide is meant that the target protein one is directing the phage or virus to bind is known. For example, a selected target can be the NMDA receptor, and therefore a ligand that can be used to detect the presence of the receptor in a sample can be, e.g., Mag-4.1 or Mag-4.2, which are shown herein to be ligands for NMDA receptor. Thus a selected polypeptide is predetermined prior to detecting the presence of the polypeptide by detecting binding of the phage or virus expressing the ligand to the polypeptide.

The virus utilized in the method can be a bacteriophage. For example the bacteriophage can be bacteriophage f1, M13, and other bacteriophages known in the art. Viruses can include any other desired virus, as will be recognized by those of skill in the art, such as adenovirus, etc. The phage or virus can be modified in any of various ways known in the art, such as to be rendered replication-deficient or to eliminate other viral genes, and methods of such modifications are standard in the art. The virus is modified to express the ligand on the surface of the virus, as by engineering the virus genome to encode a fusion protein for a coat protein and the ligand. For example, in bacteriophage, the ligand can be encoded by pIII or pVIII protein. Making bacteriophage that express peptides on their surface is standard in the art (described in e.g., U.S. Pat. No. 5,427,908; U.S. Pat. No. 5,403,484; U.S. Pat. No. 5,432,018; U.S. Pat. No. 5,432,018; U.S. Pat. No. 5,270,170; WO 92/06176; Smith et al. (1993); Kolvunen, E. et al., *J. Cell Biol.* 124:373 (1994); Kolvunen, E. et al., *Meth. ymol.* 245:346 (1994); Pasqualini, R et al. *J. Cell Biol.* 130:1189 (1995)).

The present invention includes that the protein can be a cellular protein. Cellular proteins can include intracellular proteins, extracellular proteins, and/or surface proteins. Cellular proteins as used in these methods can also include viral proteins expressed by a cell that has been infected by a virus.

The sample in which the presence of the polypeptide is detected can be a clinical sample. Clinical samples can include any relevant sample from the body, such as excised tissue, blood, plasma, urine and saliva, and protein extracts from any such sample. Other samples can include cultured cells, proteins secreted by cells, and the like.

Specific binding between an receptor or channel and a ligand means that the ligand can be used to selectively remove the receptor or channel from a sample or to inhibit the receptor or channel's function and can readily be determined by radio immune assay (RA), bioassay, or enzymelinked immunosorbant (ELISA) technology using an antibody, preferably monoclonal, specific for the ligand.

The present invention provides a method of detecting the presence of a selected polypeptide in a sample comprising contacting with the sample a detectable virus, including a bacteriophage, expressing on its surface a ligand previously demonstrated to specifically bind the selected polypeptide and detecting binding of the virus to the sample, thus detecting the presence of the selected polypeptide in the sample.

A ligand can be previously determined to specifically bind the selected protein by any known, standard means for determining such binding or, for example, as described herein. A ligand can include, for example, a peptide hormone, a toxin, a fragment from a large protein.

A detectable virus or phage is one that can be detected by any of many possible means. For example, the phage or virus can be detected by a polyclonal or monoclonal antibody directed against the virus by the antibody itself being labeled or by utilizing a secondary antibody that is labeled or has a recognition site for a label. Additionally, the phage itself can be directly detectable, as described herein.

The present invention further provides a method of detecting the presence of a selected cellular protein on the surface of a cell comprising contacting with the cell a detectable virus expressing on its surface a ligand previously demonstrated to specifically bind the selected cellular protein and detecting binding of the virus to the cell, thus detecting the presence of the selected cellular protein on the surface of the cell. Such detection includes that the cell can be in vitro or in vivo.

Conditions for contacting phage or virus with the selected polypeptide can be selected based upon the location of the target. In general, conditions for phage-receptor (or other cellular protein) binding can be as described in Sparks, A.B., et al. (1995) *Methods. Enzymol.* 255:498-509. For example, in vitro conditions for binding standard detection reagents, such as monoclonal antibodies, to cells, or for phage-receptor binding, for binding reagents to a protein blot (e.g. Li et al. (1992)), for ELISA (e.g., Barrett, et al. (1992)), for binding a reagent to a tissue sample, can be followed, with any modifications desired, particularly in light of typical conditions for binding phage libraries and in light of the examples provided herein. Additionally, in vivo conditions for contact can be determined by conditions utilized for binding, e.g., monoclonal antibodies and viruses in vivo. Virus can be administered via the bloodstream, as by intravenous administration of by administering to an artery supplying a target organ, or by direct injection into a target organ, by inhalation or intratracheal injection for delivery the lungs, and conditions can be modified accordingly such as for administration of viruses in vivo for, e.g., gene therapy.

The present invention provides a method of detecting the presence of a selected polypeptide in a sample comprising contacting with the sample a detectable bacteriophage expressing on its surface at least 10, or at least 100, or at least 400, or at least 800, or at least 1000 copies of a ligand for the selected polypeptide and detecting binding of the bacteriophage to the sample, thus detecting the presence of the selected polypeptide in the sample. Typically, by encoding the ligand within the pVIII coat protein, the ligand is expressed in high copy number. The present invention further provides a method of detecting the presence of a selected cellular protein on the surface of a cell comprising contacting with the cell a detectable bacteriophage expressing on its surface at least 10 copies, or at least 100, or at least 400, or at least 800, or at least 1000 copies of a ligand for the selected cellular protein and detecting binding of the bacteriophage to the cell, thus detecting the presence of the selected cellular protein on the surface of the cell.

The present invention further provides a method of isolating a cell expressing a selected polypeptide on its surface comprising contacting with a sample of cells a virus expressing on its surface a ligand previously demonstrated to be specific for the selected polypeptide and isolating bound virus, thereby isolating a cell expressing the selected polypeptide on its surface. The cell that binds the virus is isolated, for example, by a fluorescence activated cell sorter if the virus is labeled, either directly or indirectly, by a fluorescent moiety. For example, a cell expressing the NMDA receptor can be isolated by utilizing a virus or bacteriophage expressing of its surface Mag-4.1 or Mag-4.2.

The present invention further provides a virus, including a bacteriophage, comprising a label such that the label can be directly detected. The virus can express on its surface a ligand for a selected protein. By "directly detected" is meant that the bacteriophage can be labeled in advance and still bind its target upon addition to a cell/sample, etc. containing the target for direct detection via the label on the bacteriophage, i.e., no secondary antibody is necessary. Furthermore, by "label" is meant a means for visualization, such as a recognition site for direct phosphorylation, biotinylation, chemical linkages, etc. engineered into the virus, or such as a directly visualized label requiring no chemical reaction to detect, e.g., the virus expresses a fluorescent protein or is labeled by a radioactive moiety. Phage can be modified to include a label in advance, then bound to the phage target in a sample, and visualized to detect the presence and localization of the bound phage. Visualization may or may not require a chemical reaction. Thus, directly detected does not require interaction with a secondary labelled ligand, for example an antibody. An example of a fluorescent protein is the green fluorescent protein (GFP) originally isolated from the jellyfish *Aequorea victoria*. Another example of a fluorescent protein is the green fluorescent protein originally isolated from *Renilla reniforms*, which demonstrated a single absorption peak at 498 nm and an emission peak at 509 nm. (Cubitt, et el. (1995) TIBS 20: 448455). Phage expressing, for example, a peptide hormone, a toxin, or a fragment from a large protein can, for example, be used for a drug screening procedure.

A peptide, including a bacteriophage expressing the peptide, can be administered to a subject, including a human or an animal model, by any of many standard means for administering proteins to cells and to animal subjects. Typically, peptides can be administered orally, parenteraly (e.g., intravenously), by intramuscular injection, by intraperitoneal injection, topically, transdermally, or the like. Peptides can be administered, e.g., expressed on the surface of a bacteriophage (such as bacteriophage f1 or M13), expressed on the surface of a cell, or incorporated into a lipid composition such as a cationic liposome.

Virus or phage compositions can include various amounts of the selected virus in combination with a pharmaceutically acceptable carrier and, in addition, if desired, may include other medicinal agents, pharmaceutical agents, carriers, adjuvants, diluents, etc. Parental administration, if used, is generally characterized by injection. Injectables can be prepared in conventional forms, either as liquid solutions or suspensions, solid forms suitable for solution or suspension in liquid prior to injection, or as emulsions. (as described in e.g., Martin, E. W. (ed.) *Remington's Pharmaceutical Sciences*, latest edition Mack Publishing Co., Easton, Pa.).

To obtain a peptide ligand for a given protein target, a typical experimental paradigm involves three steps. First, phage clones carrying lead sequences are isolated from random peptide virus or phage libraries based on specific binding to the purified target protein. Second, according to the amino acid sequence information from the lead peptide sequences, mutagenised libraries can be constructed to identify homologous sequences with higher affinity. Third, based on the amino acid sequence, synthetic peptides can be obtained to directly test their affinity and activity in bioassays. Since the region or surface present in the putative functional domain may not be accessible in native receptor, it can be particularly useful to be able to evaluate binding activity of peptides present on candidate phage clones during early stage of phage selection.

As will be recognized by those skilled in the art, numerous types of immunoassays are available for use in the present invention to detect binding between a protein, such as a receptor or channel, and a peptide or other ligand of this invention. For example, a monoclonal antibody specific for the phage bearing the peptide can be contacted with the bound sample followed by secondary antibody and standard imaging. Direct and indirect binding assays, competitive assays, sandwich assays, and the like, as are generally described in, e.g., U.S. Pat. Nos. 4,642,285; 4,376,110; 4,016,043; 3,879,262; 3,852,157; 3,850,752; 3,839,153; 3,791,932; and Harlow and Lane, *Antibodies, A Laboratory Manual*, Cold Spring Harbor Publications, N.Y. (1988).

Methods of producing antibodies to detect any phage utilized herein are standard in the art (see. e.g. Harlow and Lane, *Antibodies, A Laboratory Manual*, Cold Spring Harbor Publications, N.Y. (1988).;WO 93/06213).

The examples herein show the isolation of a phage clone carrying a low affinity peptide, which specifically recognizes truncated NMDA receptor fragment. By taking advantage of the specific binding between the purified phage particles and receptor, the present invention provides phage-immunoblot, phage-immunostain, and phage-FACS procedures to monitor expression of NMDA receptor protein, or any other selected protein (with corresponding ligands on the phage), in mammalian cells. These procedures offer a new way to help monitoring receptor protein expression. In addition they can facilitate molecular characterization of the specific peptide-receptor interaction.

In order to detect an intracellular target, some modifications can be made to improve the penetration of phage particle to reach target proteins. Such improvement can involve, for example, partial disruption of phage filament to generate shorter truncated phage filaments which have better penetration but retain multivalent peptide-receptor binding Furthermore, if the specificity of phage staining is affected by the potential interaction between phage coat proteins and other cellular proteins, a phage variant with altered coat proteins that have lower background binding can readily be developed given the teachings herein. Phage variants can readily be tested for such reduced background following the methods herein.

Statement Concerning Utility

Monitoring receptor expression using recombinant bacteriophage with specific peptide ligands shares several advantages of other immunoassays. In particular, the present assays take advantage of the existing signal amplification strategies, since the binding of phage can, if desired, be eventually visualized by enzyme- or fluorescent dye-conjugated secondary antibodies that are available commercially. It is important, however, to note that there is fundamental difference between the phage-mediated immunoassay and the conventional primary antibody-mediated immunoassays. Generally, a variable region of immunoglobulin forms a binding pocket that recognizes either conformation or primary sequence of a given epitope. Because the epitope can be a very small and linear region of a protein, it is common to find that an immunoglobulin recognizes a protein in either native or denatured conformation by binding to a small embedded peptide. Conversely, the phage binding described herein requires the corresponding receptor in proper conformation to present the binding pocket for the peptide to bind. Because the conformation of receptor binding pocket is critical for the peptide binding, peptide-receptor target interaction per se can have higher specificity than that of some antibody-receptor interaction.

For peptides with interesting biological and/or therapeutic activity, it is important to understand their action in the molecular and mechanistic detail. One of the first steps to address this question is to determine the critical interacting residues on both receptor and peptides. Use of bacteriophage as a vehicle to carry multiple copies of receptor interacting peptide offers several interesting approaches for detailed molecular analysis of peptide-receptor interaction, which should be applicable to both an existing bioactive peptide (e.g., agiotensin II) or novel lead peptides (from random peptide libraries). A combination of phage-FACS analysis and random mutagenesis strategy (e.g., known strategies such as described in Rice et al., 1992) on the target receptor can offer a powerful approach to select interacting mutated receptors, which can lead to determination of interacting residues that mediate the phage-receptor interaction.

The present invention is more particularly described in the following examples which are intended as illustrative only since numerous modifications and variations therein will be apparent to those skilled in the art.

EXAMPLES

Taking advantage of high avidity resulting from the herein demonstrated specific multivalent interaction between receptor target and recombinant bacteriophage, the examples of the present invention show that a phage clone (Mag-4.1) interacting with the NH2-terminal domain of NMDARI receptor can be used to monitor the receptor expression. In the assays below, Mag-4.1 phage was used as a detecting reagent comparable to primary antibodies in immunoassays. As demonstrated in the assays described below, receptor protein can be detected on solid substrates, e.g., on nitrocellulose filters or on transfected mammalian cells. These assays offer opportunities to monitor receptor expression and access binding property profiles of selected peptides prior to more involved affinity maturation.

Isolation of the specific peptide ligand for NMDA receptor. To obtain the purified "target" protein for isolating specific peptide ligands, the putative amino-terminal domain of NR1 (N-NR1, a.a 1-561) was cloned and stably expressed in Chinese Hamster Ovary (CHO) cells as a fusion protein, in which the carboxyl-terminal portion contains an epitope tag for monoclonal antibody (mAb8610) (Whitehorn et al., 1995). Prior to panning, the N-NRI protein was treated with endo-F to remove the glycosylation and the resultant protein preparation was used as a target protein. A phage library with nine random amino peptides was constructed by inserting random oligonucleotides in frame and amino-terminal to the pVIII gene of bacteriophage f1 which encodes the major coat protein.

Figure 1:
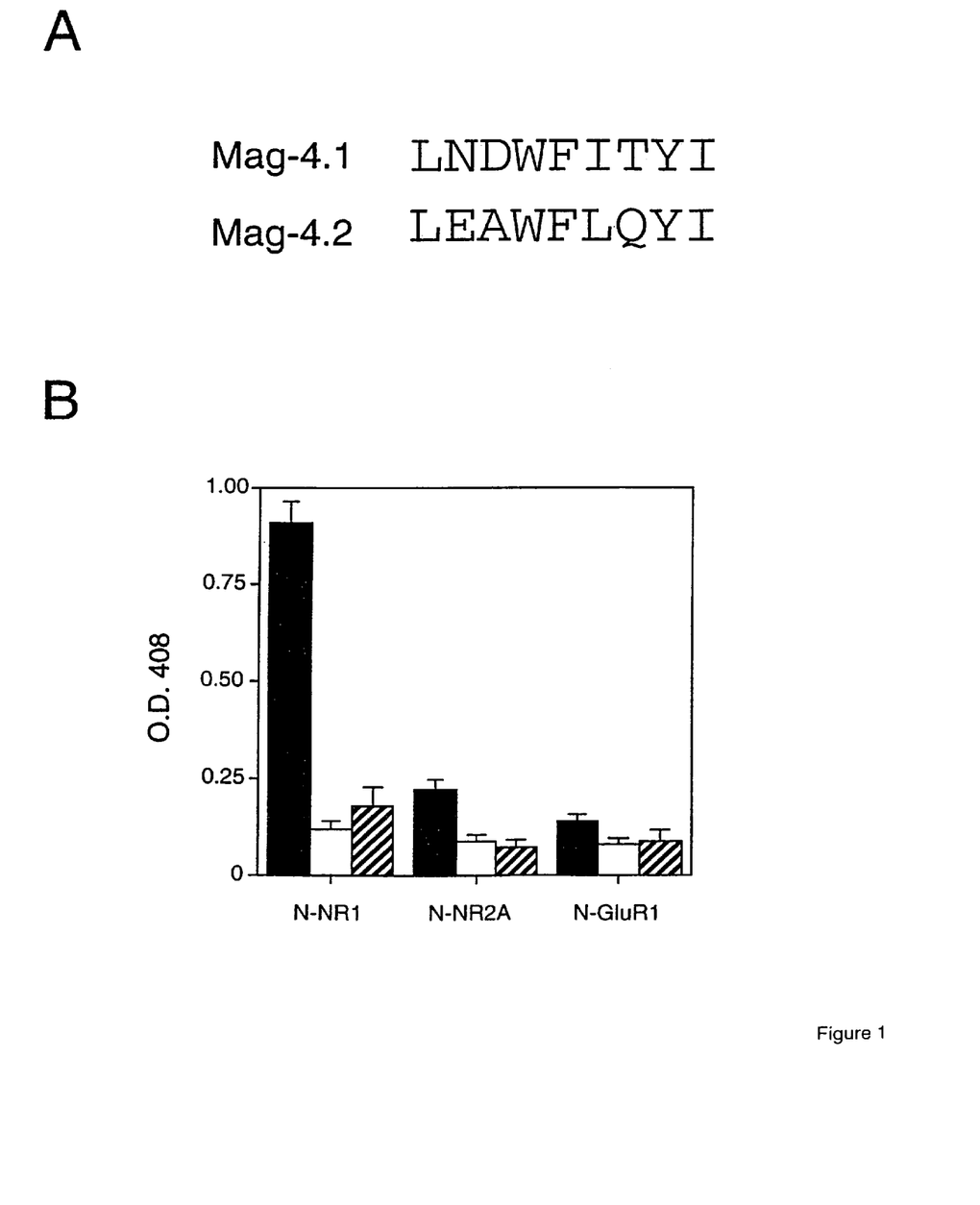

Using N-NR1 as a target protein, Mag-4 phage clone was identified from the random peptide library. After five consecutive rounds of selection and amplification, clones that specifically bind N-NR1 fusion protein were identified by testing the binding of individual phage clone to the immobilized N-NR1 (phage ELISA) (Barrett et al., 1992). Two sequence related phage clones were identified with the deduced sequences of LNDWFITYI (Mag-4.1) (SEQ ID NO:2) and LEAWFLQYI (Mag4.2) (SEQ ID NO:3). To further test the specificity of phage ELISA experiments, the phage clone of Mag4.1 was selected and used to test binding to both NH2-terminal domain of NR2A (N-NR2A, a.a 1-527), an accessory subunit that coassembles with NR1 in vivo (Nakanishi, 1992), and NH2-terminal domain of GluR1 (N-GluR1, a.a 1-431), a non-NMDA receptor with amino acid sequence homology to NR1 (Hollmann et al., 1989). FIG. 1B shows that Mag-4.1 phage binds to N-NR1, but it fails to bind NR2A or N-GluR1. This binding is specific since in the presence of 500 mM of synthetic Mag-4.1 peptide the binding of Mag-4.1 to N-NR1 was completely inhibited (FIG. 1C).

Figure 2:
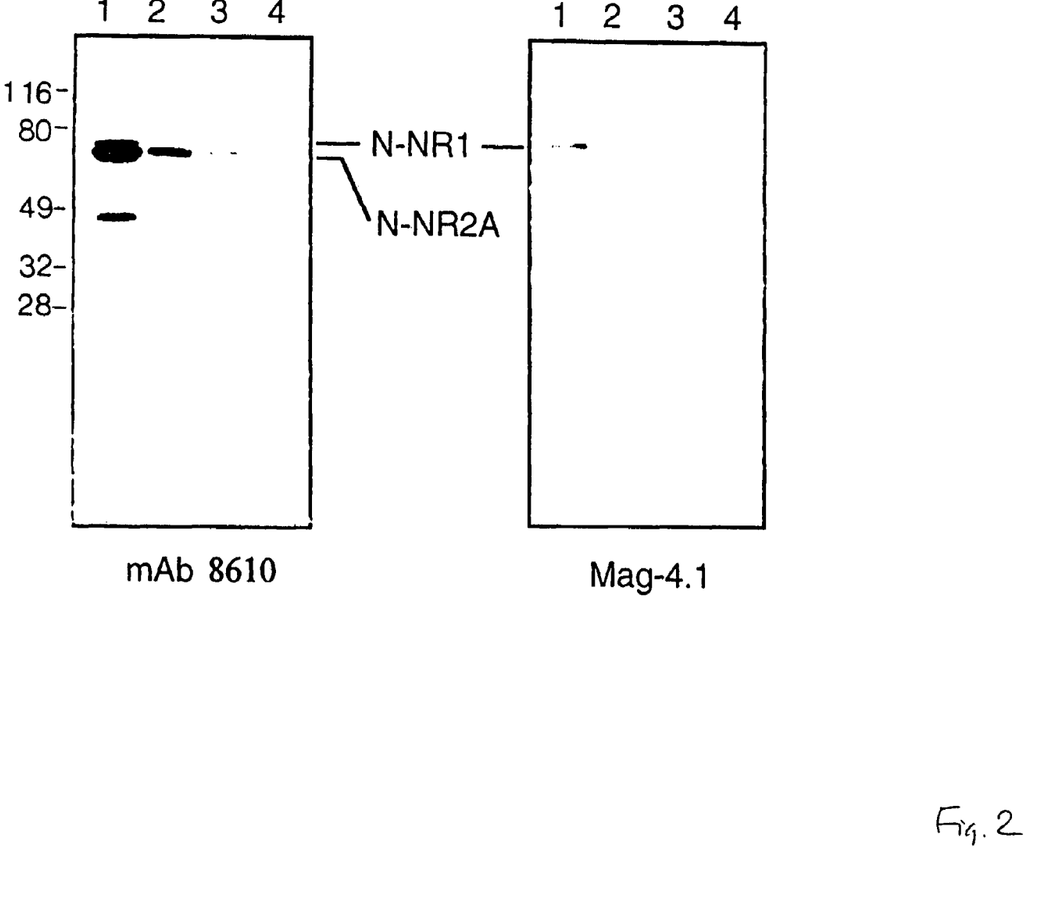

Detection of N-NR protein by phage-overlay. Monovalent Mag-4.1 peptide has low affinity (FIG. 1C). However, under the conditions of our experiments there are more than 100 copies of Mag-4.1 peptide fused with pVIII coat protein per phage particle. Thus phage particle could have high apparent affinity (avidity) due to multivalent interaction between peptide fusion protein and N-NR1. To test whether this avidity of phage-receptor interaction is sufficient for mediating specific detection, we performed "phage-overlay" assay similar to protein overlay procedure (Li et al., 1992). This binding analysis involves immobilization of target protein on nitrocellulose filter membrane with after separation by SDS-polyacrylamide gel electrophoresis. FIG. 2A shows a 5:1 mixture N-NR2A and N-NR1 fusion protein was separated by SDS-PAGE, transferred onto a nitrocellulose filter, and detected by immunoblot using the monoclonal antibody 8610 (mAb8610) (FIG. 2, left panel). To detect NR1 protein by Mag-4.1 phage, the immobilized proteins nitrocellulose filter were subjected to denaturation-renaturation procedure using guanidine-HCl (Li et al., 1992). The resultant filter was incubated with Mag4.1 phage and phage binding were visualized using anti-phage antibody. FIG. 2 (right panel) shows that Mag-4.1 phage specifically recognizes N-NR1 protein but not N-NR2A In addition, the specific binding can be detected by using as little as 20 ng (about 109 tu/ml (equivalent 10-12 M)) of N-NR1 protein per lane (FIG. 2, right panel, lane 2).

Figure 3:
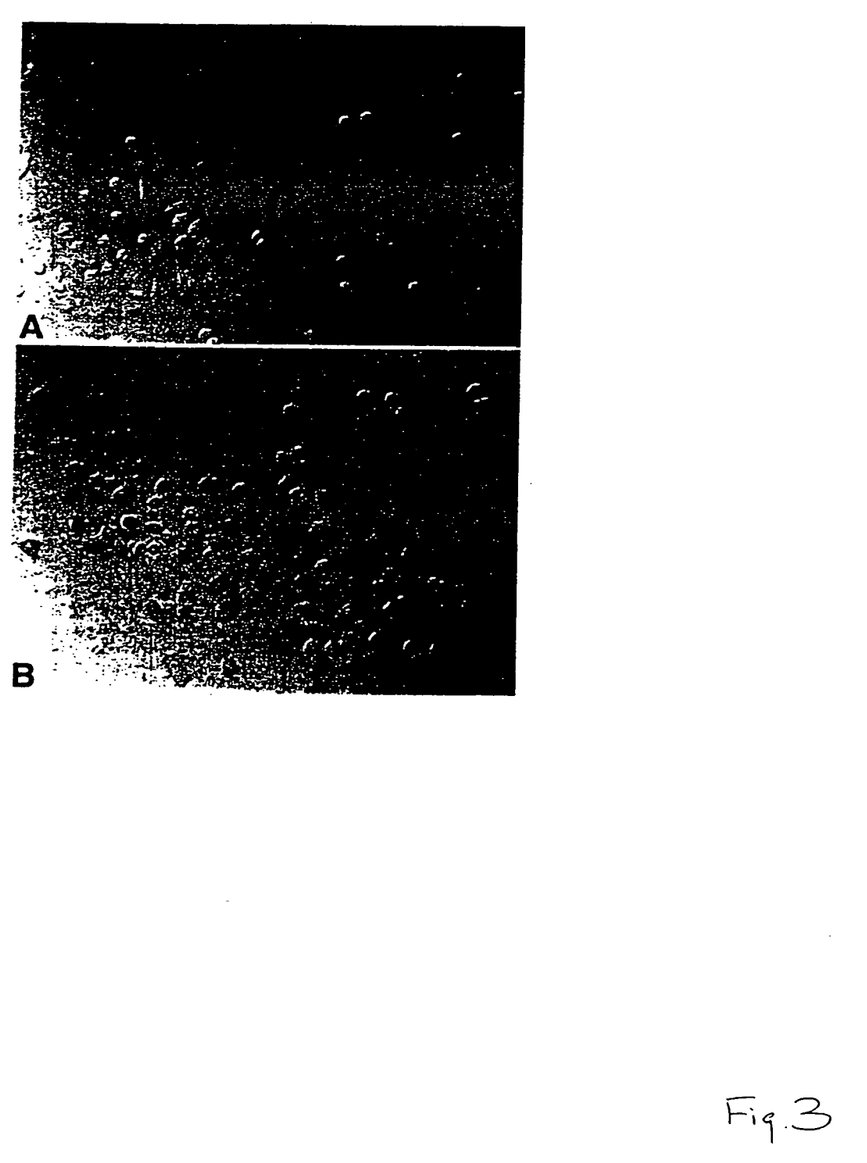
FIGS. 3A-3B. Phage-inunumostain detection of N-NR1 protein on cell surface. Two CHO cell lines expressing low ($\sim 10^4$ copies per cell) and high ($\sim 10^6$ copies per cells) of N-NR1 fusion protein were mixed by 1:1 ratio and allowed to grow on gelatin-coated cover glass. The mixed cells were incubated with Mag-4.1 phage in the presence FIG. 3A or absence FIG. 3B of 500 mM of synthetic Mag-4.1 peptide. The Mag-4.1 phage binding was detected by rabbit-anti-phage antibody (see Experimental Protocol).

Detection of N-NR1 protein by phage-immunostain. Specific detection of N-NR1 by Mag-4.1 phage (FIG. 1 and 2) suggests that phage may also be used in way similar to a primary antibody in other immunoassays. We possess two stable Chinese hamster ovary (CHO) cell lines that express N-NR1 on cell surface via GPI anchor (Caras and Weddell, 1989; Whitehom et al., 1995). These two cell lines have estimated $10^4$(low) and $10^6$ (high) copies of N-NR1 per cell. To test whether phage particle coated with specific peptide ligands can be used for immunohistochemistry detection, we incubated Mag-4.1 phage with a 1:1 mixture of the two CHO N-NR1 cell lines in the presence (FIG. 3A) or absence (FIG. 3B) of 500 mM Mag-4.1 synthetic peptide. The binding phage particles to cell surface was visualized by anti-phage antibody followed by chromogenic detection (described herein). FIG. 3A shows the phage staining on cells expressing N-NR1. The two distinctive staining intensity presumably represents the high and low density of receptor present on the two cell lines. This staining signal was completely inhibited when the phage binding was carried out in the presence of 500 mM Mag-4.1 peptide (FIG. 3B), suggesting that stain is specific to N-NR1.

Figure 4:
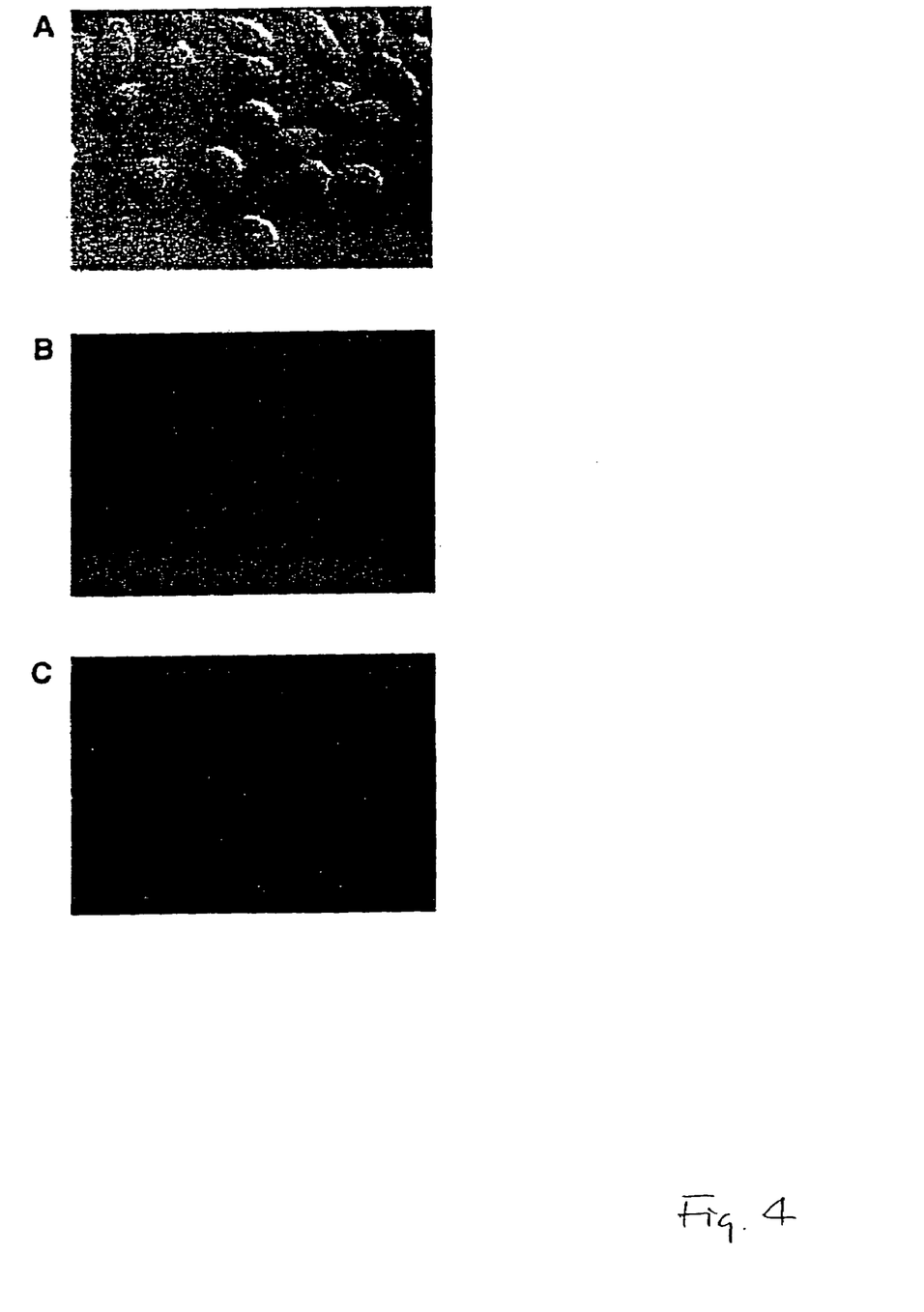

Detection of N-NR1 protein by phage-FACS. To test whether the phage-receptor interaction can be used for fluorescence staining, it is important to access the signal to noise ratio. A double staining experiment was carried out using a cell mixture containing both wildtype CHO cells and CHO cells stably expressing N-NR1. This mixture of cells was stained by mAb8610 (Texas red) and phage (fluorescein, green). FIG. 4 shows a single view of CHO cells visualized by Nomaski (FIG. 4A), mAb8610-Texas red (FIG. 4B), and phage-fluorecein (FIG. 4C). Indeed, both mAb8610 and Mag-4.1 phage stained the same subset of cells which express N-NR1.

Figure 5:
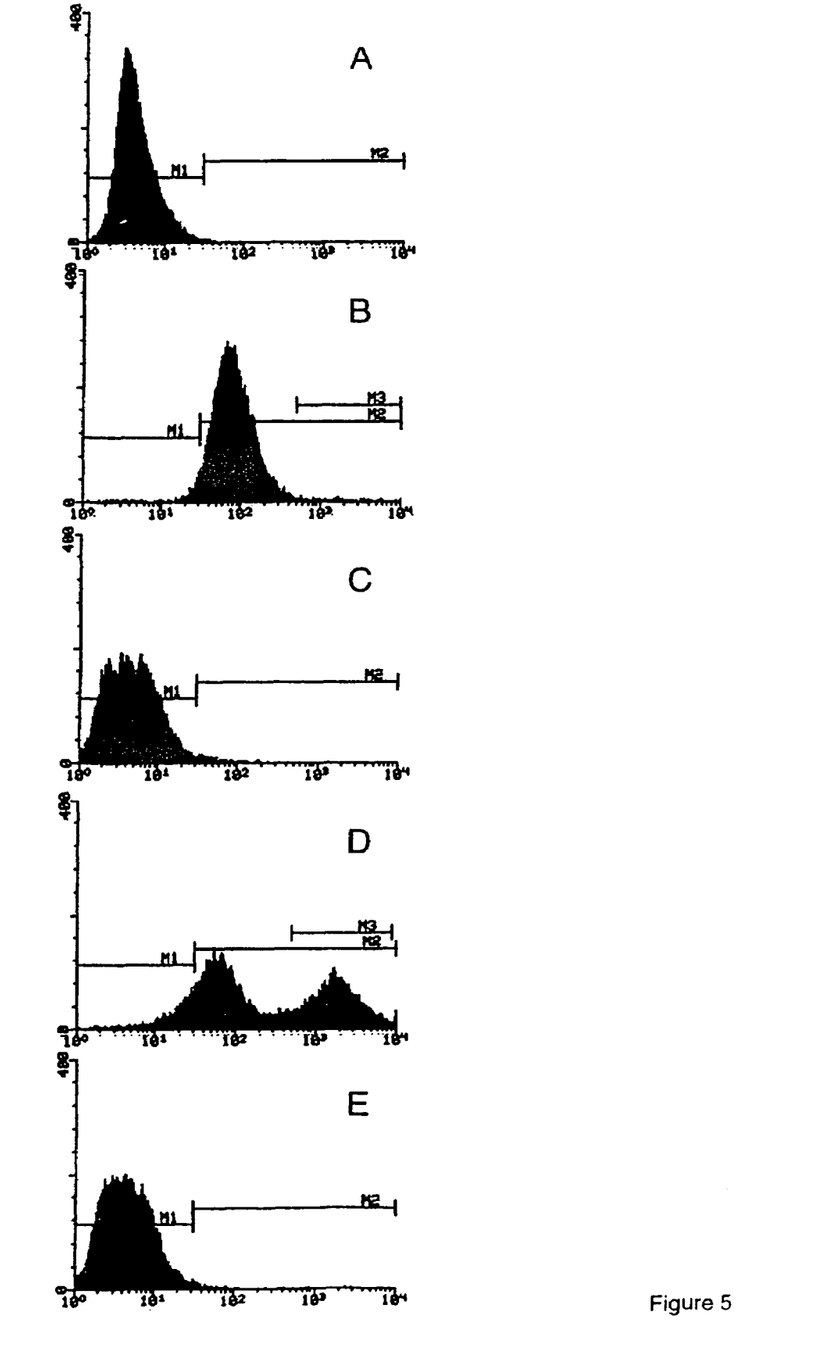

To obtain a more quantitative accessment of phage stain, fluorescence activated cell sorting (FACS) was used to detect the phage binding. FIG. 5 shows phage staining on four cell preparations: wild type CHO cells (FIG. 5A), CHO cells expressing lower N-NR1 receptor per cell (FIG. 5B), cells expressing higher N-NR1 receptor per cell (FIG. 5C), and a 1:1 mixture of them (FIG. 5D). Wild type CHO cells gave rise to background signal in Mag-4.1 phage stain (FIG. 5A). This signal is similar to the signal obtained by staining the cells with secondary antibody alone. When CHO cells with low density of N-NR1 protein were incubated with Mag-4.1 phage, elevated fluorescence signal was detected (FIG. 5B). This signal is specific, as it can be completely inhibited by the synthetic Mag-4.1 peptide (FIG. 5C). When a 1:1 mixture of CHO cells expressing low and high N-NR1 receptor was subjected to the same staining procedure, the two populations of cells were clearly separated as they have different fluorescence intensity (FIG. 5D). Similarly, the staining signal is sensitive to Mag-4.1 peptide (FIG. 5E). Together, these results show that it is feasible to use the phage-mediated fluorescence stain to detect the expression of cell surface receptor.

Dectection of intact NMDAR in cell culture. N-NR1 respresents a truncated form of NR1, an essential subunit of a pentameric NMDA receptor channel in the brain. To directly test whether Mag-4.1 phage could directly interact with an intact receptor complex, we phage-stained on HEK cells that transiently express NR1 and NR2A NMDA receptor subunits. Heteromeric assembly of NR1 and NR2A in HEK cells produces functional NMDA receptor channels with kinetic and pharmacological properties similar to what we have seen in native preparation. When experiments identical to FIG. 3 were performed on this preparation, specific Mag-4.1 phage binding signals were observed (FIGS. 5A and 5B). This staining is specific since only a sub-population of cells were stained. The ratio of stained vs unstained cells is identical to that obtained by β-galactosidase stain. In addition, in the presence of 500 mM of synthetic Mag-4.1 peptide the signal was completely inhibited.

Additional NMDA receptor (NR1) ligands (Mag peptides) isolated. The following Mag peptides were isolated, in addition to the Mag-4 peptides, by the herein described procedure for isolating specific peptide ligands, and sequence deduced:

| Peptide | Amino acid sequence | SEQ ID NO |
|---------|---------------------|-----------|
| Mag-2   | WDPAVFRGCM          | 5         |
| Mag-3   | LGSGGVQRVH          | 6         |

-continued

| Peptide | Amino acid sequence | SEQ ID NO |
|---|---|---|
| Mag-5 | MTRATPGMVF | 7 |
| Mag-6 | TNLRRGFWILL | 8 |
| Mag-7 | FSMDAWFLQYL | 9 |

Native NMDA receptors are likely to be pentameric complexes consisting of NR1 and other subunits such as NR2A. Using the putative agonist binding domain of NR1 subunit, novel peptides with modulatory activity on native NMDA receptor have been identified. Despite the purified N-NR1 receptor not being in pentamer form, it is clear that some of important structural features of NR1 are retained in the fusion protein. Additional rounds of binding using the reported approach coupled with native receptor can be performed to result in peptides with potentially even higher modulatory activity.

Methods for Labeling Phage

Bacteriophage can be modified in one or a combination of following ways to improve the detection:

(1) phage coat protein (pIII or pVIII) can be engineered to carry recognition sites to permit direct phosphorylation, biotinylation, chemical linkages, etc. to produce phage for convenient detection.

(2) phage coat protein (pIII or pVIII) can be linked to known proteins with special properties, e.g., fluorescence protein gene (e.g., green fluorescence protein) and to form a fluorescence phage variant. Such modifications would allow direct detection and enhance phage purification.

(3) phage can be prepared in medium containing radioactive precursors. Thus, the resultant phage will be radioactive.

In addition, one can engineer the phage coat to protein with specific properties which reduce the non-specific interactions between phage coat proteins and cells. Such phage variants should be a preferable generic vehicle for all phage staining experiments.

Protocols

Expression of the NH2-terminal domains of NMDA receptor. Coding sequence for N-NR1 (aa. 1-561), N-NR2A (a.a 1-527), N-NR1.sp1(a.a 1-584), and N-GluR1 (a.a. 1-431) were obtained by PCR amplification, cloned into eukaryotic cell expression vector driven by the SRa promoter, and confirmed by DNA sequencing. It was then fused in frame to a nucleotide fragment coding for "AAA-CLEPYTACDLA PPAGTTDAAHPGRSVVPALL PLLAGTLLLLETATAP" (SEQ ID NO:1), where the underlined fragment representing the tag for the monoclonal antibody 8610 (mAb8610) and remaining portion is a GPI anchor signal sequence (Caras and Weddell, 1989; Whitehorn et al., 1995). The stable transfectants were identified after 24 weeks of G418 selection (1 mg/m ). Clones with higher expression were isolated based on the fluorescence intensity and isolated using a FACS-STAR plus (Becton Dickinson). Immunohistochemical detection was carried out using mAb8610 (0.5 mg/ml) followed by 15 mg/ml of secondary antibody (Vector Labs). Imaging was performed using DAB based chromatogen according to the protocol provided by the manufacturer.

Peptide Library Construction. The filamentous phage pVIII gene was chemically synthesized using four overlapping oligonucleotides. This was inserted into the NheI and Hindm sites of the phagemid vector pBAD, which places the expression of the pVIII gene under the control of the araB promoter. A cloning site consisting of two non-complementary BstXI sites was included at the 5' end of gene VIII, and this site was used to clone collections of degenerate oligonucleotides for random nine residues (X9) using the half-site strategy as previously described (Cwirla et al., 1990). The resultant library has a complexity of $1.2 \times 10^{10}$.

Phage selection. Six wells of a 96-well plate were pre-coated with mAb8610 (5 mg/well) at 37° C. for one hour, blocked with 1% BSA for 30 minutes at 37° C. The N-NR1 fusion protein was first released by PIPLC digest after extensive washes of cells that express N-NR1. The released N-NR1 protein in the MEM medium was first treated by endo-F (1 unit per 10 mg protein) for overnight at 37° C. The treated preparation was affinity-purified by mAb8610 capture on the plates (1 mg of N-NR1 per well) at 22° C. for one hour. The phage binding was carried out by incubating with a total of $10^{12}$ tu (transducing units) of a X9 library with a complexity of $1.2 \times 10^{10}$ recombinants. The binding buffer contains 10 mM Tris-HCl (pH 8.1), 100 mM NaCl and 1 mM EDTA for 3 hours at 4° C. Unbound material was removed with three washes of the binding buffer. The bound phagemid particles were recovered by adding 100 ml of 0.1 M glycine-HCl (pH 2.2). After 10 minutes elution at room temperature, the elutes were immediately neutralized by mixing with equal volume of 0.1 M Trisbase (pH 9.2). The recovered phagemids were amplified in bacteria, and resultant phage preparations were used for the following round of purification.

After five consecutive rounds of selection, the ELISA tests were performed using the supernatant of overnight cultures in the presence of 100 mM Hepes-NaOH (pH7.5) and 100 mM NaCl. The wells were coated with receptors according to the procedure described above. The bound phage particles were first detected by using rabbit anti-phage antibody (1:10,000) followed by alkaline phosphatase (AP)-conjugated secondary antibody (1:5,000, Sigma). After washing the wells with the binding buffer, 100 ml of developing solution containing 1 mg/ml pNPP (Sigma, Mo.) in 10 mM diethanolamine-HCl (pH 9.7) was added. The alkaline phosphatase activity was monitored at the wavelength of 408 nm using a microtiter plate reader. Phage purification. The bacteria in culture medium containing phage was removed by centrifugation at 5,000×g for 30 minutes. To precipitate the phage in the resultant supernatant, 0.2 volumes of 20%/polyethyleneglycol 8000/2.5 M NaCl were added. After one hour incubation on ice, the precipitated phage was collected by centrifugation at 12,000×g for 30 minutes. The phage pellet was resuspended in 1/10 of starting culture volume and dialyzed overnight against PBS using dialysis membrane with 13 kDa cut-off. The resultant phage preparation was titered.

Immunoblot. Proteins were separated by SDS-PAGE and transferred onto a nitrocellulose membrane. The nonspecific binding to the membrane was blocked by PBS solution supplemented with 0.1% Tween20, 2% dehydrated milk, and 3% normal goat serum (ICN) for 30 minutes at room temperature. The primary antibodies used were the affinity purified monoclonal antibody 12CA5 (1:5000). The unbound material was removed by three washes with PBS solution supplemented with 0.1% Tween20. The binding of primary antibody was detected by adding corresponding peroxidase )-conjugated secondary antibody (1:5,000) followed by Enhanced ChemiLuminescence (ECL, Amersham) detection.

Phage-overlay detection. Protein lysates containing the NH2-terminal domains of glutamate receptors were fractionated by SDS-PAGE and transferred onto a nitrocellulose filter. The following steps were performed at 4 C. The filter containing immobilized proteins was first rinsed in Buffer A (10 mM Hepes-KOH, pH 7.5; 60 mM KCl; 1 mM EDTA, 1 mM 2-mercaptoethanol) for five minutes. It was then exposed for 10 minutes each to Buffer A supplemented with 6M guanidine-HCl at following concentrations: 6M, 3M, 1.5NS 0.75M, 0.38M, 0.19M, 0.1M 0M. The filter was then incubated for 60 minutes in Buffer A supplemented with 5% of carnation dry milk and 0.05% NP40. After this incubation, the filter was transferred to the same buffer except 1% carnation added. The phage binding reaction was initiated by first adding the same buffer containing Mag-1 phage with a titer $10^{10}$ tu/ml. After a 12 hour incubation, the unbound phage was removed by three 15 minute wash in Buffer A. The bound phage was detected by adding rabbit anti-phage antibody (1:5,000 dilution) in the same buffer supplemented with 1% normal goat serum and incubating for 1 hour. After three washes to remove unbound immunoglobulin, the HRP-conjugated goat anti-rabbit (Sigma, 1:5,000 dilution) was added to amplify the signals. Finally, the phage binding was detected by ECL using a procedure identical to that described in the section of Immunoblot.

Immunostain and Fluorescence Activated Cell Sorting (FACS). The cells were grown on cover glass coated with 1% gelatin. Prior to addition of immunoglobulin, the cells were first washed three times with cold PBS and fixed with 2% paraformaldehyde (PFA) overnight. After washing the cells with cold PBS, the fixed cells were incubated with mAb8610 (1 mg /ml) at room temperature for 1 hour. The binding of mAb8610 was detected by incubating with anti-mouse conjugated with Texas-red (15 mg per ml) 1 hour at 4C. The immunostain was visualized by a Nikon Optiphot-2 fluorescent microscope and images were collected/digitalized using a computer. Cytometry of stained cells were analyzed on either FACScan or FACStar Plus Sorter (Becton-Dickinson, San Jose, Calif.). An Argon laser is used and tuned at 488 nm. The green fluorescence was recorded in the FLI emission channel.

Phage-immunostain and Phage-FACS detection. The purified phage preparation was used to stain live cells. For immunostain the cells were washed three times with cold PBS. Phage binding were initiated by incubating with the cells with purified phage ($10^{10}$ tu per ml) on ice for 1 hour. After incubation, the unbound phage was removed by three washes of cold PBS supplemented with 1% bovine serum albumin (BSA). the fixation was carried out using 2% PFA overnight at 4C. The phage-binding was detected first by rabbit anti-phage antibody (1:10,000 dilution) followed by Fluorescein labeled anti-rabbit antibody (10 mg/ml, Vector Lab, Calif.). The fluorescence labeled cells were visualized under a fluorescence microscope. For Phage-FACS, the cell preparation procedures were identical except the cells were first dislodged from the dishes by incubating with PBS supplemented with 5 mM EDTA.

REFERENCES

1. Choi, D. W. 1990. Possible mechanisms limiting N-methyl-D-aspartate receptor overactivation and the therapeutic efficacy of N-methyl-D-aspartate antagonists. [Review]. *Stroke*. 21:11120-2
2. Bliss, T. V. & Collingridge, G. L. 1993. A synaptic model of memory: long-term potentiation in the hippocampus. [Review] *Nature* 361, 31-9 (1993).
3. Hollmann, M. & Heinemann, S. 1994. Cloned glutamate receptors. [Review] *Annu Rev Neurosci* 17, 31-108 (1994).
4. Monaghan, D. T., Bridges, R. J. & Cotman, C. W. 1989. The excitatory amino acid receptors: their classes, pharmacology, and distinct properties in the function of the central nervous system. [Review]. *Annu Rev Pharmacol Toxicol* 29, 365-402 (1989).
5. Nakanishi, S. 1992. Molecular diversity of glutamate receptors and implications for brain function. *Science* 258, 597-603
6. Moriyoshi K., et al. 1991. Molecular cloning and characterization of the rat NMDA receptor *Nature* 354, 31-7
7. Westbrook, G. L. & Mayer, M. L. 1987. Micromolar concentrations of $Zn_{2+}$ antagonize NMDA and GABA responses of hippocampal neurons. *Nature* 328, 640-3.
8. Johnson, J. W. and Ascher, 1987. Glycine potentiates the NMDA response in cultured mouse brain neurons. *Nature,* 325(6104): 529-31.
9. Mayer, M. L., G. L. Westbrook, and P. B. Guthrie, 1984. Voltage-dependent block by $Mg_{2+}$ of NMDA responses in spinal cord neurones. *Nature,* 309(5965): 261-3.
10. McGurk, J. F., M. V. Bennett, and R. S. Zukin, 1990. Polyamines potentiate responses of N-methyl-D-aspartate receptors expressed in xenopus oocytes. *Proc Natl Acad Sci USA,* 87(24): 9971-4.
11. Nowak, L., et al., 1984. Magnesium gates glutamate-activated channels in mouse central neurones. *Nature,* 307(5950): 462-5.
12. Peters, S., J. Koh, and D. W. Choi, 1987. Zinc selectively blocks the action of N-methyl-D-aspartate on cortical neurons. *Science,* 236(4801): 589-93.
13. Westbrook, G. L. and M. L. Maye r, 1987. Micrmolar concentrations of $Zn_{2+}$ antagonize NMDA and GABA responses of hippocampal neurons. Nature, 328(6131): 640-3.
14. Wong, E. H., et al., 1986. The anticonvulsant MK-801 is a potent N-methyl-D aspartate antagonist. *Proc Natl Acad Sci USA,* 83(18): 7104-8.
15. Lucas, D. R. and J. Newhouse, 1957. The Toxic effect of sodium L-glutamate on the inner layers of retina. *Arch Ophihalmol,* 58: 193-204.
16. Choi, D. W. and S. M. Rothman. 1990. The role of glutamate neurotoxicity in hypoxic-ischemic neuronal death. [Review]. Annu Rev Neurosci, 13: 171-82.
17. Miller, R. J., S. N. Murphy, and S. R. Glaum, 1989. Neuronal $Ca_{2+}$ channels and their regulation by excitatory amino acids. [Review]. *Ann N Y Acad Sci,* 568: 149-58.
18. Young, A. B., et al., 1983. Glutamate or aspartate as a possible neurotransmitter of cerebral corticofugal fibers in the monkey. *Neurology,* 33(11): 1513-6.
19. Rothstein, J. D., et at., 1994. Localization of neuronal and glial glutamate transporters. *Neuron,* 13(3): 713-25.
20. Rothstein, J. D., et al., 1991. Excitatory amino acids in amyotrophic lateral sclerosis: an update [letter]. *Ann Neurol,* 30(2): 224-5.
21. Rothstein, J. D., L. J. Martin, and R. W. Kuncl, 1992. Decreased glutanate transport by the brain and spinal cord in amyotrophic lateral sclerosis [see comments]. *N Eng J Med,* 326(22): 1464-8.
22. Rothstein, J. D., et al., 1993. Chronic inhibition of glutamate uptake produces a model of slow neurotoxicity. *Proc Natl Acad Sci USA,* 90(14): 6591-5.

23. Storm-Mathisen, J. and O. Ottersen, 1990. Immunocytochemistry of glutamate at the synaptic level. *J Histochem Cytochem,* 38(12): 1733-43.
24. Storm-Mathisen, J. and 0. Ottersen, 1987. Tracing of neurons with glutamate or gamma-aminobutyrate as putative transmitters. [Review]. *Biochem Soc Trans,* 15(2): 210-3.
25. O'Brien, R. J. and G. D. Fischbach, 1986. Modulation of embryonic chick motoneuron glutamate sensitivity by interneurons and agonists. *J Neurosci,* 6(11): 3290-6.
26. Tsai, G. C., et al., 1991. Reductions in acidic amino acids and N-acetylaspartylglutamate in amyotrophic lateral sclerosis CNS. *Brain Res,* 556(1): 151-6.
27. Shaw, P. J., 1994. Excitotoxicity and motor neurone diseases: a review of the evidence. *J. Neurological Sci.,* 124: 6-13.
28. Johnson, J. W. and Ascher, 1987. Glycine potentiates the NMDA response in cultured mouse brain neurons. *Nature,* 325(6104): 529-31.
29. Smith, G. P., 1985. Filamentous fusion phage: novel expression vectors that display cloned antigens on the virion surface. *Science,* 228(4705): 1315-7.
30. Scott, J. K. and G. Smith, 1990. Searching for peptide ligands with an epitope library. *Science,* 249(4967): 386-90.
31. Cwirla, S. E., et al., 1990. Peptides on phage: a vast library of peptides for identifying ligands. *Proc Natl Acad Sci USA,* 1990. 87(16): 6378-82.
32. Devlin, J. J., L. C. Panganiban, and P. E. Devlin. 1990. Random peptide libraries: a source of specific protein binding molecules. *Science,* 249(4967): 404-6.
33. Caras, I. W. & Weddell, G. N. 1989. Signal peptide for protein secretion directing glycophospholipid membrane anchor attachment. Science 243, 1196-8 (1989).
34. Chazot, P. L., Cik, M. & Stephenson, F. A. 1992. Immunological detection of the NMDARI glutamate receptor subunit expressed in embryonic kidney 293 cells and in rat brain. *J Neurochem* 59, 1176-8.
35. Barrett, R. W., et al., 1992. Selective enrichment and characterization of high affinity ligands from collections of random peptides on filamentous phage. *Anal Biochem,* 204(2): p. 357-64.
36. Haack, J. A., et al., 1990. Conantokin-T. A gammaoxyglutamate containing peptide with N-methyl-d-aspartate antagonist activity. *J Biol Chem,* 265(11): 6025-9.
37. Huettner, J. E. and B. P. Bean, 1988. Block of N-methyl-D-aspartate-activated current by the anticonvulsant MK-801: selective binding to open channels. *Proc Nad Acad Sci USA,* 85(4): p. 1307-11.
38. Mori, H., et al., 1992. Identification by mutagenesis of a $Mg_{(2+)}$-block site of the NMDA receptor channel. *Nature,* 358(6388): 673-5.
39. Monyer, H., et al., 1992 Heteromeric NMDA receptors: molecular and functional distinction of subtypes. *Science,* 256(5060): 1217-21.
40. Kutsuwada, T., et al. 1992. Molecular diversity of the NMDA receptor channel [see comments]. *Nature,* 358 (6381): 36-41.
41. Tingley, W. G., et al, 1993 Regulation of NMDA receptor phosphorylation by alternative splicing of the C-terminal domain. *Nature,* 1993. 364(6432): 70-3.
42. Cilk, M., P. L. Chazot, and F. A. Stephenson. 1993. Optimal expression of cloned NMDAR1/NMDAR2A heteromeric glutamate receptors: a biochemical characterization. *Biochem J,* 1993. 296(Pt 3): 877-83.
43. Li, M., Jan, Y. N. & Jan, L. Y. 1992. Specification of subunit assembly by the hydrophilic amino-terminal domain of the Shaker potassium channel. *Science* 257, 1225-30.
44. Blond-Elguindi, S., Cwirla, S. E., Dower, W. J., Lipshutz, D. J., Sprang, S. R, Sambrook, J. F., and Gething, M. J. (1993). Affinity panning of a library of peptides displayed on bacteriophages reveals the binding specificity of BiP. Cell 75, 717-28.
45. Dedman, J. R, Kaetzel, M. A., Chan, H. C., Nelson, D. J., and Jamieson, G., Jr. (1993). Selection of targeted biological modifiers from a bacteriophage library of random peptides. The identification of novel calmodulin regulatory peptides. *J Biol Chem* 268, 23025-30.
46. Greenamyre, J. T., Penney, J. B., Young, A. B., D'amato, C. J., Hicks, S. P., and Shoulson, I. (1985). Alterations in L-glutamate binding in Alzheimer's and Huntington's diseases. Science 227.
47. Hollmann, M., O'Shea-Greenfield, A., Rogers, S. W., and Heinemann, S. (1989). Cloning by functional expression of a member of the glutamate receptor family. Nature 342, 643-8.
48. Kay, B. K., Adey, N. B., He, Y. S., Manfredi J. P., Mataragnon, A H., and Fowlikes, D. M. (1993). An M13 phage library displaying random 38-amino-acid peptides as a source of novel sequences with affinity to selected targets. Gene 128, 59-65.
49. Rice, G. C., Goeddel, D. V., Cachianes, G., Woronicz, J., Chen, E. Y., Williams, S. R, and Leung, D. W. (1992). Random PCR mutagenesis screening of secreted proteins by direct expression in mammalian cells. Proc. Natl. Acad. Sci. USA 89, 5467-5471.
50. Sparks, A. B., Quilliam, L. A, Thorn, J. M., Der, C. J., and Kay, B. K. (1994). Identification and characterization of Src SH3 ligands from phage-displayed random peptide libraries. *J Biol Chem* 269, 23853-6.
51. Whitehorn, E. A, Tate, E., Yanofsky, S. D., Kochersperger, L., Davis, A, Mortensen, R. B., Yonkovich, S., Bell, K, Dower, W. J., and Barrett, R. W. (1995). A generic method for expression and use of "tagged" soluble versions of cell surface receptors. Biotechnology 13, 1215-1219.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof it is not intended that such details should be regarded as limitations upon the scope of the invention except as and to the extent that they are included in the accompanying claims.

What is claimed is:

1. A method of detecting the presence of a selected cellular protein on the surface of a cell using a detectable, recombinant virus expressing a ligand on its surface which binds to the cellular protein, comprising:

contacting the cell with a population of the detectable virus, each virus expressing on its surface the ligand, wherein the ligand expressed on the surface of the virus comprises a peptide comprising an amino acid sequence selected from the group consisting of SEQ ID NO: 2 and SEQ ID NO: 3; and detecting binding of the virus to the cell, thus detecting the presence of the selected cellular protein on the surface of the cell, wherein the cellular protein is N-methyl D-aspartate receptor.

2. A method of detecting the presence of a selected cellular protein on the surface of a cell using a detectable, recombinant virus expressing a ligand on its surface which binds to the cellular protein, comprising:

contacting the cell with a population of the detectable virus, each virus expressing on its surface the ligand; and detecting binding of the virus to the cell, thus detecting the presence of the selected cellular protein on the surface of the cell, wherein the ligand expressed on the surface of the virus comprises a peptide comprising an amino acid sequence selected from the group consisting of SEQ ID NO: 2 and SEQ ID NO: 3.

3. A method of detecting the presence of a selected cellular protein on the surface of a cell using a detectable, recombinant bacteriophage expressing a ligand on its surface which binds to the cellular protein, comprising:

contacting the cell with a population of the detectable bacteriophage, each bacteriophage expressing on its surface at least 10 copies of the ligand for the selected cellular protein, wherein the ligand expressed on the surface of the bacteriophage comprises a peptide comprising an amino acid sequence selected from the group consisting of SEQ ID NO: 2 and SEQ ID NO: 3 and detecting binding of the bacteriophage to the cell, thus detecting the presence of the selected cellular protein on the surface of the cell, wherein the cellular protein is N-methyl D-aspartate receptor.

4. A method of detecting the presence of a selected cellular protein on the surface of a cell using a detectable, recombinant bacteriophage expressing a ligand on its surface which binds to the cellular protein, comprising:

contacting the cell with a population of the detectable bacteriophage, each bacteriophage expressing on its surface at least 10 copies of the ligand for the selected cellular protein: and detecting binding of the bacteriophage to the cell, thus detecting the presence of the selected cellular protein on the surface of the cell, wherein the ligand expressed on the surface of the bacteriophage comprises a peptide comprising an amino acid sequence selected from the group consisting of SEQ ID NO: 2 and SEQ ID NO: 3.

* * * * *